(12) United States Patent
Kecht et al.

(10) Patent No.: US 10,013,835 B2
(45) Date of Patent: Jul. 3, 2018

(54) SECURITY FEATURE AND USE THEREOF, VALUE DOCUMENT AND PROCESS FOR VERIFYING THE AUTHENTICITY THEREOF

(71) Applicant: GIESECKE & DEVRIENT GMBH, München (DE)

(72) Inventors: Johann Kecht, München (DE); Martin Stark, München (DE)

(73) Assignee: GIESECKE+DEVRIENT CURRENCY TECHNOLOGY GMBH, Munich (DE)

( * ) Notice: Subject to any disclaimer, the term of this patent is extended or adjusted under 35 U.S.C. 154(b) by 0 days.

(21) Appl. No.: 15/120,309

(22) PCT Filed: Feb. 18, 2015

(86) PCT No.: PCT/EP2015/000359
§ 371 (c)(1),
(2) Date: Aug. 19, 2016

(87) PCT Pub. No.: WO2015/124295
PCT Pub. Date: Aug. 27, 2015

(65) Prior Publication Data
US 2017/0076530 A1    Mar. 16, 2017

(30) Foreign Application Priority Data

Feb. 19, 2014    (DE) .................. 10 2014 002 271
Nov. 10, 2014    (DE) .................. 10 2014 016 858

(51) Int. Cl.
*G07D 7/12*     (2016.01)
*D21H 21/48*    (2006.01)
(Continued)

(52) U.S. Cl.
CPC .............. *G07D 7/12* (2013.01); *B42D 25/21* (2014.10); *B42D 25/29* (2014.10); *B42D 25/378* (2014.10);
(Continued)

(58) Field of Classification Search
CPC .... B42D 25/29; B42D 25/382; B42D 25/387; D21H 21/48; G07D 7/12; G07D 7/00
See application file for complete search history.

(56) References Cited

U.S. PATENT DOCUMENTS 4,452,843 A    6/1984  Kaule et al.
8,153,984 B2   4/2012  Olm et al.
(Continued)

FOREIGN PATENT DOCUMENTS

DE    102004027416 A1    12/2005
DE    102011122240 A1     6/2013
(Continued)

OTHER PUBLICATIONS

International Search Report from corresponding PCT Application No. PCT/EP2015/000359, dated May 12, 2015.
(Continued)

*Primary Examiner* — Marcus Taningco
(74) *Attorney, Agent, or Firm* — Workman Nydegger

(57) ABSTRACT

The invention relates to a security feature for safeguarding value documents, comprising particles which are composed of at least two different, spatially separate solid homogeneous phases, wherein each of the phases is detectable and identifiable in a spatially resolved manner by means of a spatially resolving analytical method that is adapted for resolving down to the single-particle level.

25 Claims, 1 Drawing Sheet

(51) Int. Cl.
| | |
|---|---|
| *B42D 25/382* | (2014.01) |
| *B42D 25/378* | (2014.01) |
| *G07D 7/2033* | (2016.01) |
| *B42D 25/21* | (2014.01) |
| *B42D 25/29* | (2014.01) |
| *B42D 25/387* | (2014.01) |
| *G01N 21/64* | (2006.01) |
| *G07D 7/1205* | (2016.01) |

(52) U.S. Cl.
CPC ......... *B42D 25/382* (2014.10); *B42D 25/387* (2014.10); *D21H 21/48* (2013.01); *G01N 21/6428* (2013.01); *G07D 7/1205* (2017.05); *G07D 7/2033* (2013.01)

(56) References Cited

U.S. PATENT DOCUMENTS

| | | | |
|---|---|---|---|
| 9,327,542 B2 | 5/2016 | Kecht et al. | |
| 9,540,771 B2 | 1/2017 | Giering et al. | |
| 9,540,772 B2 | 1/2017 | Kecht | |
| 9,542,788 B2 | 1/2017 | Kecht | |
| 2003/0132538 A1 | 7/2003 | Chandler | |
| 2004/0022684 A1* | 2/2004 | Heinze | B82Y 10/00 |
| | | | 422/82.08 |
| 2008/0163994 A1 | 7/2008 | Hoppe et al. | |
| 2008/0251581 A1 | 10/2008 | Faenza | |
| 2011/0018252 A1 | 1/2011 | Petry et al. | |
| 2012/0175528 A1 | 7/2012 | Haubrich et al. | |
| 2012/0326055 A1* | 12/2012 | Wilson | A61B 5/0059 |
| | | | 250/459.1 |
| 2013/0009119 A1* | 1/2013 | Natan | B82Y 30/00 |
| | | | 252/582 |
| 2014/0367958 A1 | 12/2014 | Giering et al. | |
| 2015/0276601 A1* | 10/2015 | Giering | B42D 25/29 |
| | | | 283/92 |
| 2015/0328915 A1 | 11/2015 | Kecht et al. | |
| 2016/0215456 A1 | 7/2016 | Kecht | |
| 2016/0232735 A1 | 8/2016 | Kecht | |

FOREIGN PATENT DOCUMENTS

| | | |
|---|---|---|
| DE | 102012013244 A1 | 1/2014 |
| EP | 0927750 A1 | 7/1999 |
| WO | 8103507 A1 | 12/1981 |
| WO | 2006072380 A2 | 7/2006 |
| WO | 2007031077 A1 | 3/2007 |
| WO | 2009071167 A2 | 6/2009 |
| WO | 2010048535 A1 | 4/2010 |
| WO | 2010138914 A1 | 12/2010 |
| WO | 2012094108 A1 | 7/2012 |
| WO | 2015043760 A2 | 4/2015 |
| WO | 2015043761 A2 | 4/2015 |

OTHER PUBLICATIONS

International Preliminary Report on Patentability from corresponding PCT Application No. PCT/EP2015/000359, dated Aug. 23, 2016.

* cited by examiner

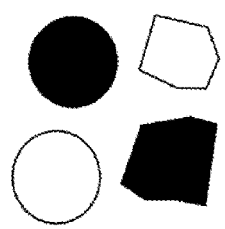
FIG 1(a)
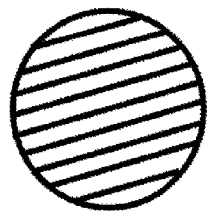
FIG 1(b)
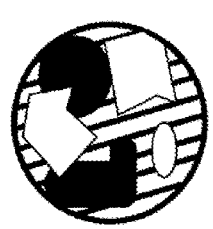
FIG 1(c)
FIG 2
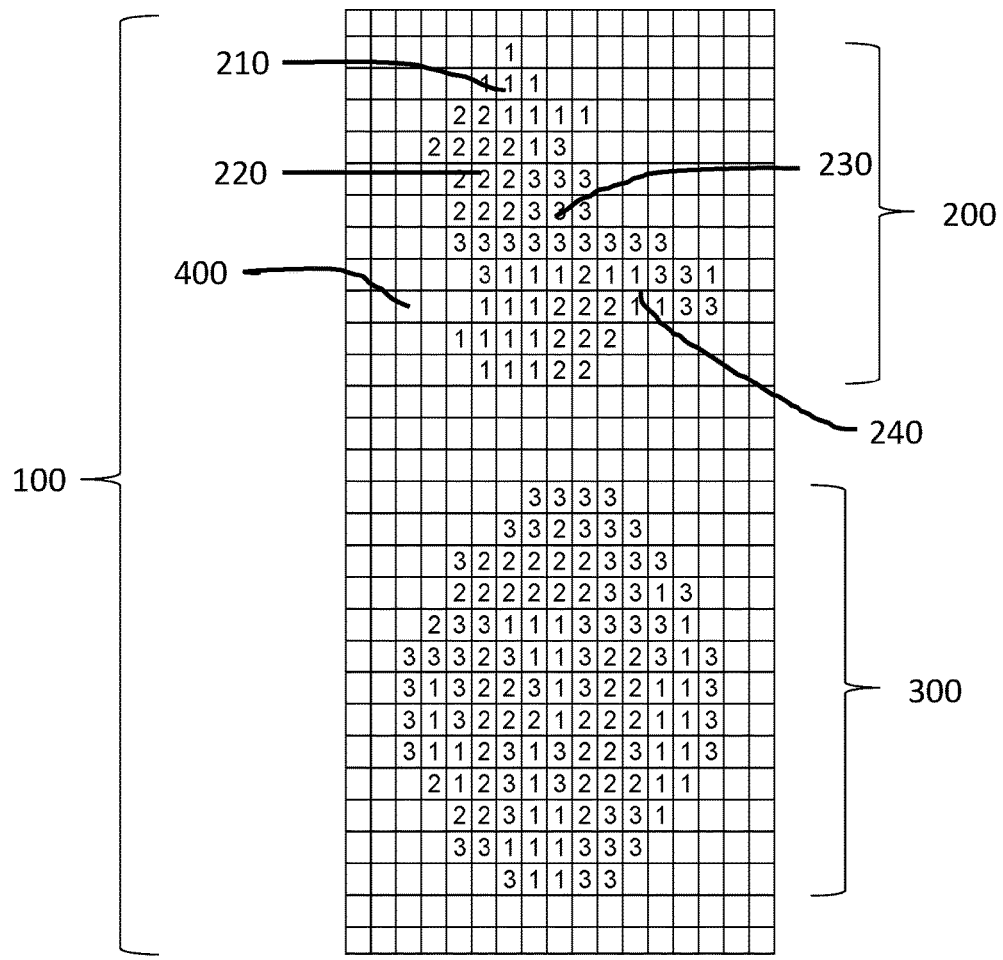

SECURITY FEATURE AND USE THEREOF, VALUE DOCUMENT AND PROCESS FOR VERIFYING THE AUTHENTICITY THEREOF

BACKGROUND

This invention relates to a security feature for safeguarding value documents, a value document, in particular a bank note, having such a security feature, a method for checking the authenticity of the value document by analyzing single particles of the security feature by spatially resolved microscopic methods (hereinafter also designated as "forensic methods") and a use of the security feature for safeguarding a value document.

The safeguarding of value documents against forgery by means of security features has been known for some time. Feature substances are known that are based e.g. on magnetic, thermal, electrical and/or optical (e.g. absorption and emission) effects, through which the specific detectability is guaranteed.

DE 10 2012 013 244 A1 describes a value document having luminescing, particulate agglomerates which each contain at least two different luminescing, solid homogeneous phases emitting at first and second emission wavelengths, respectively. By means of the agglomeration of two luminescent pigments in one particle there is effectuated a correlation of their luminescence intensities at different measuring sites of the value document. The method for checking the presence of a value document comprises, more precisely, the following steps:
a) exciting the luminescing substances to emission;
b) capturing measurement values in a macroscopically location-resolved and wavelength-selective manner for the radiation emitted by the luminescing substances, there being produced for each of the first and the second emission wavelength measurement-value pairs involving emission wavelength and location, to thereby obtain first luminescence intensities at the first emission wavelength and second luminescence intensities at the second emission wavelength;
c) checking whether a statistical correlation is present between the first luminescence intensities and the second luminescence intensities.

However, this print does not describe forensic security features (i.e. security features whose authentication is based on the analysis of single particles by spatially resolved microscopic methods) in which the substructure of individual feature substance particles is detected and identified in a spatially resolved manner by means of spatially resolved analytical techniques (such as spatially resolved X-ray diffraction, spatially resolved Raman scattering, energy-dispersive X-ray spectroscopy or spatially resolved X-ray fluorescence analysis).

US 2012/0175528 A1 describes a particulate composition having particles of which at least one particle contains at least two different crystalline phases and/or glass phases. Each phase comprises a host lattice and a dopant sensitive to electromagnetic radiation. The luminescence emission of the individual luminescing phases yields a well-defined mixed signal as a result of the agglomeration. However, the relatively homogeneously constructed agglomerates described in this prior art are unsuitable as a forensic security feature. The agglomerates are manufactured by a special spray-drying process. The individual phase regions of the different luminescent pigments in the agglomerate are hereby very small, i.e. sometimes only a few nanometers in size, with the total particle size amounting to <10 µm. The agglomerates as a whole thereby appear to be constructed homogeneously, so to speak, which is advantageous for use as a mixed-signal emitting luminescent pigment as intended in the print US 2012/0175528 A1. Upon use as a forensic security feature as intended by the present application, however, one can no longer detect any spatially clearly separate regions for the two kinds of luminescent pigment. The agglomerate can therefore not, or not readily, be distinguished from an individual luminescent pigment emitting a luminescence signal that is identical or similar to the mixed signal.

WO 2009/071167 A2 describes a forensic marking of paints, plastics, etc., with a security pigment consisting of colorant particles embedded in an inorganic transparent matrix. For detecting the forensic marker, first the outer shape and size of the security pigment and then the color or shape, size and number of the embedded colorant particles are determined under the microscope. Here, the wide availability of microscopes as the aid used for detection has an adverse effect on the security of the marking, since the essential aspects of the marking can be easily recognized in the case of a forgery attack.

US 2003/0132538 A1 describes the encapsulating of two or more fluorescence carriers for different applications. There are furthermore described a plurality of applicable analytical methods, including a "luminometer microscope". However, no security features are described in this print.

The print WO 2010/048535 A1 describes a VIS-VIS feature system based on a luminophore mixture in which the two mixture components can be distinguished by their specific excitation spectrum. However, neither are agglomerates used, nor forensic analyses at the single-particle level carried out.

The print WO 2012/094108 A1 describes porous polymer particles for toners or security applications, which are loaded in the individual pores with a plurality of distinguishable, in particular fluorescent, radioactive or IR-absorbent markers. The pore size amounts to 20 nm to 4 µm, the particle size 2 µm to 75 µm. However, no forensic analyses at the single-particle level are described.

The print WO 2010/138914 A1 describes the combination of SERS nanoparticles with luminescent substances, magnetic substances and substances with a distinguishable mass spectrum or XRF spectrum, wherein the combination is effectuated via an encapsulation, e.g. in a silica shell. However, no forensic analyses at the single-particle level are discussed.

The invention is based on the object of providing a security feature improved with regard to anti-forgery security, and a value document furnished with such a security feature. A further object is to provide a method for checking the authenticity of the value document.

This object is achieved by the feature combinations defined in the main claims. Preferred embodiments are the subject matter of the subclaims.

SUMMARY OF THE INVENTION 1. (First aspect of the invention) A security feature for safeguarding value documents, comprising particles (hereinafter also designated as "agglomerate particles" or "composite particles") which are composed or agglomerated from at least two different, spatially separate solid homogeneous phases (hereinafter also designated as "primary particles"), wherein each of the phases is detectable and identifiable in a spatially resolved manner by means of a spatially resolving analytical method that is adapted for resolving down to the single-particle level.

Preferred embodiment: A security feature for safeguarding value documents, comprising particles (hereinafter also designated as "agglomerate particles" or "composite particles") which are composed or agglomerated from at least two different, spatially separate solid homogeneous phases (hereinafter also designated as "primary particles"), wherein each of the phases is detectable, separable and identifiable in a spatially resolved manner only by means of a spatially resolving spectroscopic measuring method that is adapted for resolving down to the single-particle level. The spatially resolving spectroscopic measuring method is in particular able to detect with resolution in all three spatial directions.

2. (Preferred embodiment) The security feature according to item 1, wherein the at least two different, spatially separate solid homogeneous phases comprise luminescing substances which preferably emit in the visible spectral region.

3. (Preferred embodiment) The security feature according to item 1 or 2, wherein the luminescing substances have a different excitation wavelength.

4. (Preferred embodiment) The security feature according to any of items 1 to 3, wherein the composite particles are selected from the group consisting of pigment agglomerates, encapsulated pigment agglomerates, nanopigment-encased pigments and core/shell particles.

5. (Preferred embodiment) The security feature according to any of items 1 to 4, wherein the composite particles have a D99 grain size in a range of 1 micrometer to 30 micrometers, preferably in a range of 5 micrometers to 20 micrometers, further preferably in a range of 10 micrometers to 20 micrometers, and in particular preferably in a range of 15 micrometers to 20 micrometers.

6. (Preferred embodiment) The security feature according to any of items 1 to 5, wherein the composite particles have a D50 grain size in a range of 1 micrometer to 30 micrometers, preferably in a range of 5 micrometers to 20 micrometers, and in particular preferably in a range of 7 micrometers to 20 micrometers.

7. (Preferred embodiment) The security feature according to any of items 1 to 6, wherein the solid homogeneous phases composing the composite particles respectively have a (D99) grain size in a range of 3 micrometers to 15 micrometers, preferably in a range of 4 micrometers to 10 micrometers, and in particular preferably in a range of 5 micrometers to 9 micrometers.

8. (Preferred embodiment) The security feature according to any of items 1 to 7, wherein the solid homogeneous phases composing the composite particles respectively have a (D50) grain size in a range of 1 micrometer to 8 micrometers, preferably in a range of 1.2 micrometers to 5 micrometers, and in particular preferably in a range of 1.5 micrometers to 3 micrometers.

9. (Preferred embodiment) The security feature according to any of items 1 to 8, wherein the composite particles are composed of two different, spatially separate solid homogeneous phases of which the first homogeneous phase is based on a first luminescing substance and the second homogeneous phase is based on a second luminescing substance, wherein the two luminescing substances have different rise times and/or decay times.

10. (Preferred embodiment) The security feature according to any of items 1 to 9, wherein the luminescing agglomerate particles are so constituted that the luminescence emission of each individual phase is sharp-band and the luminescence emission of each individual phase preferably has a complex spectrum consisting of at least two sharp bands, there further being preferred an emission spectrum in the range of 400 to 750 nm, there being in particular preferred an emission spectrum in the range of 550 to 750 nm. Further specifically, the complex spectra of the individual phases mutually overlap, i.e. are not congruent but differ in their shape, namely, peak position and/or peak shape and/or peak width in a range of 1 nm to 30 nm, further preferably 2 nm to 20 nm, in at least two bands per phase.

11. (Preferred embodiment) The security feature according to any of items 1 to 9, wherein the composite particles are composed of two different, spatially separate solid homogeneous phases of which the first homogeneous phase is based on a first luminescing substance and the second homogeneous phase is based on a second luminescing substance, wherein the two luminescing substances have the same emission wavelengths but different excitation wavelengths and/or decay times and/or rise times. Preferably, the first and second luminescing substances differ merely in their dopings.

12. (Preferred embodiment) The security feature according to any of items 1 to 11, wherein the composite particles are composed of two different, spatially separate solid homogeneous phases of which the first homogeneous phase is based on a first luminescing substance with a rise time >2 µs, preferably >10 µs, in particular preferably >20 µs.

13. (Preferred embodiment) The security feature according to any of items 1 to 12, wherein the composite particles are composed of two different, spatially separate solid homogeneous phases of which the first homogeneous phase is based on a first luminescing substance and the second homogeneous phase is based on a second luminescing substance, wherein the two luminescing substances have the same luminescence properties but mutually differ with regard to their elemental compositions.

14. (Preferred embodiment) The security feature according to any of items 1 to 13, wherein additionally at least one camouflaging substance is added which does not consist of composite particles itself and has similar properties to the agglomerate particles under the analytical method utilized for detection, and in particular in the case of a luminescing agglomerate particle with sharp-band emission in a certain spectral region has broad-band luminescence in said spectral region.

15. (Second aspect of the invention) A value document, in particular a bank note, having a security feature according to any of items 1 to 14.

16. (Preferred embodiment) The value document according to item 15, wherein the security feature is incorporated into the volume of the value document and/or applied to the value document.

17. (Preferred embodiment) The value document according to item 15 or 16, wherein the share of the security feature in the value document lies in a range of 0.001 to 0.1 percent by weight, preferably in a range of 0.003 to 0.05 percent by weight, and in particular preferably in a range of 0.005 to 0.05 percent by weight.

18. (Preferred embodiment) The value document according to any of items 15 to 17, wherein the composite particles are contained in the value document with an area density such that in the particle-size range of 4 micrometers to 20 micrometers there are contained particle numbers of 1 to 1000 particles per square millimeter, preferably 1 to 100 particles per square millimeter, in particular preferably 1 to 30 particles per square millimeter.

19. (Third aspect of the invention) A method for checking the authenticity of the value document according to any of items 15 to 18, comprising the step of spatially resolved detecting, separating and identifying of the at least two different, spatially separate solid homogeneous phases contained in the composite particles by means of at least one spatially resolving spectroscopic measuring method that is adapted for resolving down to the single-particle level and reliably separating the phases spectrally.

20. (Preferred embodiment) The method according to item 19, wherein the spatially resolving analytical method is selected from the group consisting of confocal laser microscopy, multiphoton microscopy, fluorescence lifetime microscopy (FLIM), spatially resolved X-ray diffraction (μXRD), spatially resolved Raman scattering (μRaman), scanning electron microscopy with energy-dispersive X-ray spectroscopy (SEM/EDX) and spatially resolved X-ray fluorescence analysis (μXRF).

21. (Fourth aspect of the invention) A method for safeguarding a value document, comprising the following steps:
    a) predetermining at least one spatially resolving spectroscopic measuring method;
    b) selecting at least two solid homogeneous phases having at least one property distinguishable by the spatially resolving spectroscopic measuring method;
    c) combining the at least two solid homogeneous phases into composite particles;
    d) incorporating and/or applying the composite particles into or onto the value document as a security feature;
    e) detecting the substructure of the composite particles in a spatially resolved manner and reliably separating the spectroscopic properties of the homogeneous phases by means of the predetermined spatially resolving spectroscopic measuring method;
    f) rating the authenticity of the value document using the data obtained in step e).

22. (Preferred embodiment) The method according to item 21, wherein the security feature is defined according to any of items 1 to 14.

23. (Fifth aspect of the invention) Use of the security feature according to any of items 1 to 14 as a forensic security feature in a value document (i.e. for value-document authentication based on the analysis of single particles by spatially resolved microscopic, spectroscopic methods), in particular a bank note, wherein the share of the security feature in the value document lies in a range of 0.001 to 0.1 percent by weight, preferably in a range of 0.003 to 0.05 percent by weight, and in particular preferably in a range of 0.005 to 0.05 percent by weight.

24. (Preferred embodiment) The use according to item 23, wherein the composite particles are contained in the value document with an area density such that in the particle-size range of 4 micrometers to 20 micrometers there are contained particle numbers of 1 to 1000 particles per square millimeter, preferably 1 to 100 particles per square millimeter, in particular preferably 1 to 30 particles per square millimeter.

25. (Sixth aspect of the invention) A value-document system having at least first value documents (e.g. of a first denomination) containing first composite particles and second value documents (e.g. of a second denomination) containing second composite particles, wherein the first and second composite particles are respectively defined according to any of items 15 to 18, wherein the first and second value documents can be distinguished on the basis of at least one of the spatially separate solid homogeneous phases by one or more predetermined spatially resolving spectroscopic measuring methods.

26. (Preferred embodiment) The value-document system according to item 25, wherein the distinguishable properties are selected from luminescence emission wavelength, luminescence excitation wavelength, time behavior of the luminescence, elemental composition, in particular EDX signature, three-dimensional form, in particular aspect ratio, isotope ratio, oscillation spectrum, in particular IR or Raman spectrum, crystal structure, magnetic properties.

BRIEF DESCRIPTION OF THE DRAWINGS

FIG. 1(a) is a comparative example showing a mixture of particles with a first luminescence property (black) and particles with a second luminescence property (white).

FIG. 1(b) is a further comparative example showing a particle that shows both the first luminescence property and the second luminescence property at every particle position uniformly (illustrated in the figure by a uniform, hatched area).

FIG. 1(c) illustrates an embodiment example according to the invention showing a particle that shows the first luminescence property, the second luminescence property or mixed signals of first and second luminescences in dependence on the location.

FIG. 2 shows schematically a digitized photomicrograph of two agglomerate particles according to the invention respectively having a plurality of signal regions in the form of individual pixels or contiguous pixel regions.

DETAILED DESCRIPTION OF THE INVENTION

Value documents within the context of this invention are objects such as bank notes, checks, shares, value stamps, identity cards, passports, credit cards, deeds and other documents, labels, seals, and objects to be safeguarded such as jewelry, CDs, packages and the like. The value-document substrate need not necessarily be a paper substrate, but might also be a plastic substrate or a substrate having both paper constituents and plastic constituents. The preferred area of application is bank notes that are in particular based on a paper substrate.

Forensic security features are known in the prior art. In the present description, forensic security features are understood to be so-called "microspectroscopic security features" or security features that are detectable and identifiable by means of spectroscopic measurement techniques based on spatially resolved single-particle examination, such as spatially resolved X-ray diffraction, spatially resolved Raman scattering, spatially resolved luminescence spectroscopy, energy-dispersive X-ray spectroscopy or spatially resolved X-ray fluorescence analysis. The print WO 2007/031077 A1 describes the use of special diatoms in product protection. The diatoms can be identified in the microscope on the basis their specific shell structures. Further, the print EP 0 927 750 B1 describes the determination of the elemental ratios in a single particle via SEM/EDX, e.g. by means of a scanning electron microscope, as an encoding method for security markers.

The use of luminescing markers as microscope-based security features is also known. For example, the print U.S. Pat. No. 8,153,984 B2 describes the use of luminescing particles with a specific size distribution for safeguarding different articles.

The present invention is based on the idea of authenticating a value document by drawing on the spatially resolved, spectroscopic measurement of a specific property at the single-particle level on a composite particle (or agglomerate particle). The specific property preferably relates to the luminescence behavior with measurable properties such as excitation wavelength, emission wavelength, intensity of emission, rise time or decay time, etc. Further measurable properties are also conceivable, such as elemental composition, Raman signal, etc.

According to the invention, it is indicated using a predetermined analytical method on an individual particle that the particle is composed of different solid homogeneous phases with different properties, wherein the phases respectively form a spatially extensive region in the particle. Such particles can be distinguished by means of a suitable analytic measurement method from a mixture of single particles which respectively only indicate a property of an individual phase, or from homogeneous mixed particles which respectively indicate both properties of both phases. In dependence on the selected measurement method and the particulate composition, the composite particles forming the security feature according to the invention can also have mixed signals with different shares of the properties of the first and second phases. However, it is characteristic that such ratios change depending on the position on the particle, and that within the particle there are larger contiguous regions in which the first or second property respectively dominates. In particular a variation of the properties in the particle along all three spatial directions is advantageous. This means that, in the particles according to the invention, changes occur between accordingly distinguishable phases preferably along all three spatial directions. This allows an improved identification of the particles independently of their currently present orientation. In addition, it ensures that a mixed signal is respectively measured for the arbitrarily oriented particles by a non-spatially resolving analytical method. This behavior is represented schematically in FIG. 1.

FIG. 1(a) is a comparative example showing a mixture of particles with a first luminescence property (black) and particles with a second luminescence property (white). FIG. 1(b) is a further comparative example showing a particle that shows both the first luminescence property and the second luminescence property at every particle position uniformly (illustrated in the figure by a uniform, hatched area). FIG. 1(c) illustrates an embodiment example according to the invention showing a particle that shows the first luminescence property, the second luminescence property or mixed signals of first and second luminescences in dependence on the location.

For example, in FIG. 1 the first property that is associated with the first homogeneous phase (black areas) may be a luminescence with a band in the red spectral region at 620-630 nm, and the second property that is associated with the second homogeneous phase (white areas) a luminescence in the red spectral region at 625-645 nm. Areas filled in with hatching luminesce simultaneously in both (overlapping) spectral regions. The mixture shown in FIG. 1(a) is thus a simple mixture of the two illuminants. FIG. 1(b) shows an individual illuminant which luminesces simultaneously in both spectral regions. The composite particle shown in FIG. 1(c) likewise shows luminescence in both spectral regions but possesses spatially separate regions in which luminescence in one of the two spectral regions respectively predominates or mixed forms of significantly different shares of the two luminescences occur. In the case of non-flat particles, such separation of the different spatially separate regions is only possible when the spectroscopic measuring method measures in a spatially resolved manner in all three spatial directions. Otherwise only a mixed spectrum of the different contributions from the homogeneous phases will generally be detected through the superimposition in the third dimension.

In a further example, the property changing within the particle relates to the elemental composition of the two homogeneous phases. In this case, the black areas shown in FIG. 1 might contain one or more elements, e.g. zinc, white areas other elements, e.g. aluminum, and hatched areas both elements, e.g. zinc and aluminum. In this case, the particles in FIG. 1(a) would be e.g. a mixture of zinc oxide and aluminum oxide, the particles in FIG. 1(b) a zinc-aluminum spinel, and the particles in FIG. 1(c) a solid agglomerate of zinc-oxide and aluminum-oxide particles.

Preferably, the agglomerate particles of the security feature according to the invention comprise a plurality of inorganic materials, in particular they consist only of inorganic materials.

It is further preferred that the particles of the security feature according to the invention are luminescing feature substances, in particular with emissions in the visible spectral region. The individual, luminescing, solid homogeneous phases forming the composite particles (or particulate agglomerates or agglomerate particles) of the security feature can be based e.g. on an inorganic solid forming a matrix and doped with one or more rare earth metals or transition metals. Suitable inorganic solids that are suitable for forming a matrix are for example:

oxides, in particular tri- and tetravalent oxides such as titanium oxide, aluminum oxide, iron oxide, boron oxide, yttrium oxide, cerium oxide, zirconium oxide, bismuth oxide, as well as more complex oxides such as garnets, including, inter alfa, e.g. yttrium iron garnets, yttrium aluminum garnets, gadolinium gallium garnets; perovskites, including, inter alfa, yttrium aluminum perovskite, lanthanum gallium perovskite; spinels, including, inter alfa, zinc aluminum spinels, magnesium aluminum spinels, manganese iron spinels; or mixed oxides such as ITO (indium tin oxide);

oxyhalides and oxychalcogenides, in particular oxychlorides such as yttrium oxychloride, lanthanum oxychloride; as well as oxysulfides, such as yttrium oxysulfide, gadolinium oxysulfide;

sulfides and other chalcogenides, e.g. zinc sulfide, cadmium sulfide, zinc selenide, cadmium selenide;

sulfates, in particular barium sulfate and strontium sulfate;

phosphates, in particular barium phosphate, strontium phosphate, calcium phosphate, yttrium phosphate, lanthanum phosphate, as well as more complex phosphate-based compounds such as apatites, including, inter alfa, calcium hydroxyl apatites, calcium fluorapatites, calcium chlorapatites; or spodiosites, including e.g. calcium fluorospodiosites, calcium chlorospodiosites;

silicates and aluminosilicates, in particular zeolites such as zeolite A, zeolite Y; zeolite-related compounds such as sodalites; feldspars such as alkali feldspars, plagioclases; further inorganic compound classes such as vanadates, germanates, arsenates, niobates, tantalates.

Alternatively, the individual, luminescing, solid homogeneous phases forming the composite particles of the security feature can also be based on a plurality of matrix-forming inorganic solids which are doped with one or more rare earth metals or transition metals, as long as there is present within each phase a homogeneous property that can be drawn on for the authentication according to the invention.

As doping elements for the accordingly suitable matrix materials there are used in particular Sm, Pr, Eu, Mn, Dy, Tb, Ce, Ag, or Cu in order to form phases luminescing in the visible spectral region. It is particularly preferred to use Mn, Sm, Pr, Eu for luminescence in the red spectral region, Tb, Mn, Dy, Ce for luminescence in the yellow-green spectral region, and Tb, Ce, Eu for luminescence in the blue spectral region. In the composite particles of the security feature there are advantageously used different luminescing phases with doping elements selected from an individual color group, in the same or in different matrix materials. Alternatively, the composite particles of the security feature can combine different luminescing phases which contain the same doping element in different matrix materials and have emission spectra. Thus, the encoding of the security feature is more difficult to discover, since the optical impression suggests uniformly luminescing particles.

The luminescing particles (see for example FIG. 1(c)) that are preferably used in the security feature of the present invention have greatly elevated security compared to the mixture of single substances shown in FIG. 1(a) and the homogeneous particles shown in FIG. 1(b). For example, they cannot be imitated by a simple mixture of two dopants in a matrix. Further, there can also be used those combinations of dopants that cannot be used simultaneously in a single matrix e.g. due to energy-transfer effects (e.g. quenching processes). Since the kind of matrix can likewise exert a strong effect on the luminescence properties, it is likewise possible in the case of composite particles to obtain, through a suitable choice of the matrices, combinations of luminescence properties that are not possible in a single matrix.

Due to the manufacturing process, the individual phases do not necessarily contribute to the individual agglomerate particles in a fixed ratio. This means in particular that for individual examined agglomerate particles the two signal intensities obtained by a certain (e.g. microscopic) measurement method, which are due to the two phases of the particle, are not necessarily in a predetermined ratio. Such a predetermined signal ratio would only come about upon a macroscopic detection with averaging over a great number of single agglomerates. For example, an agglomerate particle of a value document marked according to the invention might have five regions that can be associated with the first homogeneous phase of the particle, and have only two regions that can be associated with the second homogeneous phase. A further agglomerate particle of the marked value document might have two regions per homogeneous phase. A third agglomerate particle might have a region that can be associated with the first homogeneous phase of the agglomerate particle, wherein the area of the region is twice as large as that of a second region that can be associated with the second homogeneous phase.

To guarantee an absolutely certain identification of a composite agglomerate particle, it is advantageous that the spatial regions of the first and second homogeneous phases are accordingly large. A particle composed of constituents that are too small will appear spatially homogeneous upon analysis and consequently not be able to be distinguished from an "authentic" homogeneous particle unambiguously, or only with high effort. Hence, the detected regions, the composite agglomerate particles and the single constituents for manufacturing the composite agglomerate particles of the security feature according to the invention preferably have certain minimum sizes.

It is preferred that the composite particles have a (D99) grain size in a range of 1 to 30 μm, further preferably in a range of 5 to 20 μm, yet further preferably in a range of 10 to 20 μm, and in particular preferably in a range of 15 to 20 μm.

In a preferred embodiment, the agglomerate particles have a three-dimensionally extended form, in particular a spheroidal or fractal arrangement. The aspect ratio of the greatest to the smallest extension of the agglomerate particles amounts here to less than 1:2, preferably less than 1:1.8, particularly preferably less than 1:1.5. Therefore, the agglomerate particles have no areal places where the composition would already be directly observable, but rather they can only be analyzed by three-dimensionally resolving methods with accordingly complex equipment. When said particles are viewed without three-dimensional resolution, only a mixed color of the individual phases will therefore be perceived or measured. This considerably improves the anti-forgery security of the security feature.

Independently of the above D99 grain sizes or in addition to the above D99 grain sizes, the composite particles preferably have a (D50) grain size in a range of 1 to 30 μm, further preferably in a range of 5 to 20 μm, and in particular preferably in a range of 7 to 20 μm.

The D99 and D50 values stated in the present print are based on measurements of the hydrodynamic diameter using industrial-standard grain-size determination instruments such as of the trademark "CILAS", which determine grain-size distributions of the particles suspended in a liquid by light scattering. The terms D99 and D50 designate that 99% and 50% of the particles, based on the volume-weighted grain-size distribution curve, are smaller than or equal to the stated value.

The primary particles or pigments embodying the different homogeneous phases and composing the agglomerate particles preferably have a (D99) grain size in a range of 3 to 15 μm, further preferably in a range of 4 to 10 μm, and in particular preferably in a range of 5 to 9 μm. Independently thereof or additionally thereto, the (D50) grain size of the primary particles or pigments of which the agglomerate particles are composed is preferably in a range of 1 to 8 μm, further preferably in a range of 1.2 to 5 μm, and in particular preferably in a range of 1.5 to 3 μm.

By adhering to the above preferred grain-size relations one can obtain especially advantageous composite particles. On the one hand, the composite particles contain larger particle regions consisting of a single homogeneous phase (essentially determined by the D99 grain-size value of the individual primary particles or pigments of which the agglomerate particles are composed) that are well separable and identifiable by microscopic spectroscopic methods as intended by the invention. On the other hand, the composite particles contain particle regions consisting of a single homogeneous phase that, upon the comparative analysis of different individual agglomerate particles, lead to distinctly varying ratios of the signals of the first and second homogeneous phases (essentially determined by the D50 grain-size value of the individual primary particles or pigments of which the agglomerate particles are composed). The D99 grain-size values of the individual primary particles or pigments of which the agglomerate particles are composed should be neither too high relative to the size of the agglomerate particles (elevated probability of obtaining larger particles consisting of a single homogeneous phase) nor too low (the particle regions in the agglomerate particle that consist of a single homogeneous phase become too small for reliable analysis). Likewise, the D50 grain-size value of the individual primary particles or pigments of which the agglomerate particles are composed should not be smaller than 1 micrometer. At grain sizes of the primary particles of less than 1 micrometer, the different, solid homogeneous phases can no longer be reliably identified spatially separately upon the microscopic analysis of the agglomerate particles by the preferred analytical methods (such as spatially resolved X-ray diffraction, spatially resolved Raman scattering, energy-dispersive X-ray spectroscopy or spatially resolved X-ray fluorescence analysis). Thus, the different phases are no longer reliably separable.

The composite particles are preferably produced by agglomerating small primary particles or single pigments while simultaneously coating with a silica shell (see e.g. WO 2006/072380 A2).

In a preferred embodiment, the individual primary particles are held together with a thin layer of a strongly scattering inorganic binder. The layer thickness of the binder amounts to 20 nm to 4 µm, preferably 30 nm to 2 µm, particularly preferably 40 nm to 1 µm. The scattering binder can be formed by sintering inorganic nanoparticles of e.g. $SiO_2$ with dimensions in the range of 10 nm to 100 nm. The binder has a scattered-light component (haze) of 25%-60%, preferably 30%-50%, particularly preferably 35%-45%, in the spectral region of the excitation radiation. This accordingly reduces the direct transmission of the binder to <75%, preferably <70%, particularly preferably <65%. However, in the case of luminescing primary particles the light scattering in the particle improves the effective cross section for the excitation radiation since now, instead of the primary-particle area, the close surroundings thereof also effectively contribute to the excitation. However, the scattering effect of the binder must not be too high—at least in the spectral region of the emitted radiation—so as not to excessively impair the spatially resolved detection of the emitted radiation and still enable the signals of the different primary particles to be reliably separated.

To further increase the security, agglomerate particles can be formed of two different particles having a first common property, so that the agglomerate particles only prove to be an agglomerate upon spatial examination of a second property. In the case of luminescing particles, the first property can be the emission spectrum, while the second property is the time behavior of the luminescence emission. This includes the rise time and/or decay time.

For example, a red luminescing illuminant with a first decay time can be agglomerated with a likewise red luminescing illuminant with an emission spectrum that is very similar or even identical in the red, but a different second decay time. The agglomerate particles act like homogeneous particles upon superficial viewing of the emission. Upon more precise spatially resolved examination of the decay time, the different regions within the agglomerate particle that have first and second decay times can be identified (e.g. by means of "FLIM", i.e. fluorescence lifetime imaging microscopy).

It is particularly preferred in this connection that at least one phase has a luminescence lifetime and/or luminescence rise time that corresponds approximately to the pixel integration time or longer. In particular preferred are decay times >20 µs, preferably >100 µs, particularly preferably >500 µs, and rise times >2 µs, preferably >10 µs, particularly preferably >20 µs. This considerably impedes the discovery of the luminescing phase in scanning microscopic methods, since accordingly long pixel integration times must be used to achieve a sufficiently great signal-noise margin relative to the background.

According to a further embodiment, the agglomerate particles can be composed of illuminants that have the same (or similar) emission wavelengths but possess different excitation spectra. By variation of the excitation one can identify the different regions in the agglomerate particle.

As luminescing substances it is also possible to use upconverters, i.e. substances in which the excitation is effected at a higher wavelength than the emission.

According to a further embodiment, the agglomerate particles can be composed of particles that have the same (or similar) luminescence properties but differ with regard to the elements of their respective matrix. In this connection (since in this case the differences in the elemental composition are crucial) it is irrelevant whether the luminescence is emitted in the visible or in the invisible spectral region. For example, the two substances $Y_2O_2S$:Yb and $Gd_2O_2S$:Yb are hardly distinguishable in their luminescence behavior. Agglomerate particles consisting of said two substances act like a uniform illuminant upon spectral viewing and can be used as a machine-readable feature. Upon a forensic, that is, spatially resolved, analysis of the elemental constituents, however, one recognizes separate regions containing yttrium and gadolinium, respectively.

To further increase the security, there can be added to the security feature a camouflaging substance which has similar properties to the agglomerate particles and occurs in distinctly higher concentration. For example, an agglomerate particle with sharp-band emission in a spectral region can be camouflaged by the addition of relatively large amounts of a camouflage substance consisting of particles with broad-band luminescence in the same spectral region. Upon superficial analysis of the value document a plurality of particles luminescing in the corresponding spectral region will be found, most of which are not the feature. If the exact emission spectrum of the feature is known, however, the latter can be isolated from the plurality of further found particles e.g. by an automated search function.

Alternatively or additionally, adding the camouflage substance can be effected such that it is embedded in the agglomerate particles of the security feature. For example, two illuminants with sharp-band emission in a spectral region can be incorporated within an agglomerate particle together with an illuminant with broad-band emission in the same spectral region, superimposing the sharp bands. The additional, broad-band emitting illuminant is admixed as a camouflage substance in the form of single particles. Upon superficial analysis, merely the broad-band luminescence in the corresponding spectral region is found. Only a high-resolution measurement shows the existence of the narrow-band components in the case of agglomerate particles.

In a variant of the embodiment described in the above paragraph, the actual feature components in the agglomerate particle are so constituted that they can only be distinguished using the fluorescence lifetime (by means of "FLIM", i.e. fluorescence lifetime imaging microscopy).

When luminescing agglomerate particles are used, the luminescence emission is preferably sharp-band, the luminescence emission further preferably having a complex spectrum consisting of at least two sharp bands, there further being preferred an emission spectrum in the range of 400 to 750 nm (i.e. the detector range of a conventional confocal laser microscope), there being in particular preferred an emission spectrum in the range of 550 to 750 nm (this avoids the natural luminescing background in value documents based on a cotton substrate).

Further specifically, the complex spectra of the individual phases mutually overlap, i.e. are not congruent but differ in their shape, namely, peak position and/or peak shape and/or peak width in a range of 1 nm to 30 nm, further preferably 2 nm to 20 nm, in at least two bands per phase.

This achieves the result that the luminescence of the individual phases cannot be reliably distinguished on the basis of the color impression by simple visual viewing, even using a microscope, where applicable. Consequently, it is considerably more difficult to recognize the fact that different phases or luminescence emission is present. A reliable mutual separation of the individual phases can only be effected here by a quantitatively measuring spectroscopic method that resolves the existing differences.

According to a further preferred embodiment, the luminescence emission of the luminescing agglomerate particles is preferably sharp-band, the luminescence emission preferably has a complex spectrum consisting of a plurality of sharp bands, further preferred is an emission spectrum in the range of 750 nm to 3000 nm.

The two illuminants combined in a luminescing agglomerate particle preferably have disjoint excitation spectra or partly disjoint excitation spectra, that is, they can be excited separately from each other. Particularly preferably, they additionally have at least one common excitation wavelength, so that they are excitable both separately and jointly.

According to a further embodiment, the illuminants combined into an agglomerate particle have strongly overlapping excitation spectra (particularly preferably the same excitation spectra) and differ in the luminescence lifetime while having substantially the same emission spectrum.

According to a further embodiment, the illuminants combined into an agglomerate particle have strongly overlapping excitation spectra (particularly preferably the same excitation spectra) and differ in parts of the emission spectrum.

Preferably, the properties of the single substances composing the agglomerate particle are so selected that, if the respective specific signal is known, the spatially resolved total signal can be divided into the respective shares (preferably in an automated manner via an algorithm). Via the spatially resolved measurement of the shares of the single signals in the total signal (for example spectral composition, luminescence lifetime or element frequency) the property of a composite particle can then be detected. A composite particle is present when locations where a signal component dominates (e.g. preferably more than a 50% share of said signal component in the total signal, further preferably more than a 60% share, in particular preferably more than a 75% share) can be combined into a contiguous domain and when for each single component at least one such domain exists and when said domains of the single components are contiguous and/or separated only by a contiguous domain with the mixed signal of the components. As intended by the invention, an above-mentioned domain is sufficiently extensive when, upon application of the selected analytical method, it is imaged by a sufficient number of pixels to enable a reliable association of the signal. The required domain size depends on the analytical technique and its resolution. For this description it is preferred, following ISO 16323 sections 7 and 8, that the pixel size in the case of composite particles corresponds to at least one fifth of the D99 value of the primary particle size (i.e. the size of the single particles or primary particles composing the agglomerate particle), and that the physical resolving power of the utilized detection technique accordingly likewise corresponds to at least one fifth of the D99 value of the primary particle size. Preferably, a rateable region consists of at least five pixels contiguous via their edges, particularly preferably of at least ten contiguous pixels.

FIG. 2 shows schematically a digitized photomicrograph (100) of two agglomerate particles (200, 300) according to the invention respectively having a plurality of signal regions in the form of individual pixels (400) or contiguous pixel regions (210, 220, 230, 240). These can be respectively associated (210, 220) with one of the spatially separate, different, solid homogeneous phases or constitute (230) mixed signals of first and second phase properties, which cannot be unambiguously associated. By way of example, a signal region (240) is also marked that comprises only four pixels ("1") and hence does not satisfy the required detection condition. In the figure the digit "1" designates the region of the first homogeneous phase, the digit "2" the region of the second homogeneous phase, and the digit "3" the region of the mixed signal phase.

Further preferably, said domains must have an extension that is greater than the D99 value of the primary particle size distribution, further preferably greater than 0.5 µm, further preferably greater than 1 µm and in particular preferably greater than 2 µm. This description also holds analogously for three-dimensionally resolved domains.

The particles of the security feature according to the invention are used in particular for marking value documents. It is preferred that the particles are incorporated homogeneously into the paper substrate of the value document, e.g. a bank note. Alternatively, the particles can be a constituent of a printing ink or of another part of the value document, e.g. a constituent of a foil security element applied to the value document, such as a patch or strip.

The preferred share of security feature in the value document is in the range of 0.001 to 0.1 percent by weight, particularly preferably 0.003 to 0.05 percent by weight, in particular preferably 0.005 to 0.03 percent by weight.

Preferably, the particles are contained in the value document in an area density such that in the particle-size range of 4 µm to 20 µm there are contained particle numbers of 1 to 1000 particles per square millimeter, further preferably 1 to 100 particles per square millimeter, in particular preferably 1 to 30 particles per square millimeter.

Upon detection of the particles it should be heeded that for example SEM/EDX is restricted by the excitation depth to near-surface regions, while technologies such as confocal microscopy capture a thin layer around the focal plane. This means that usually only a fraction of the actually contained feature particles can be detected at one device setting and/or sample preparation.

According to a preferred embodiment, the composite particles can be combined as a forensic security feature with a machine-readable security feature. One can thereby realize three kinds of authentication: (1) only the machine-readable feature is drawn on; (2) only the forensic security feature is detected; (3) both the machine-readable feature and the forensic security feature are detected (simultaneously or successively).

Preferably, the machine-readable features are substances luminescing in the invisible spectral region (in particular UV or NIR). The composite particles according to the invention are admixed to the machine-readable security feature in particular in a small amount and applied to the value document jointly therewith. The share of composite particles in the mixture with the machine-readable feature is preferably in the range of 0.2 to 20 percent by weight, further preferably in the range of 1 to 10 percent by weight, and in particular preferably in the range of 2 to 6 percent by weight (based on the total amount of the machine-readable feature and of the agglomerate particles).

The forensic security feature can, in so doing, be for example utilized to verify, or have verified, the absolutely certain authenticity of the value document without knowing or revealing details about the spectroscopic properties and the readout of the machine-readable feature.

It is preferred to evaluate an optical property as a measurable property of the different homogeneous regions in the agglomerate particle, e.g. by measuring the spatially resolved luminescence spectrum in a confocal laser microscope. Particularly preferably, the agglomerate particles are so constituted that the different phases within the agglomerate particle cannot be reliably distinguished by visual viewing, even in a fluorescence microscope. In this connection it is in particular to be noted that slight variations in color, luminescence intensity, etc., are usually already observable from primary particle to primary particle in agglomerates of primary particles of a single phase, so that a visual assessment would require accordingly strongly different primary particles.

Further preferred is a check of the elemental composition of the individual homogeneous regions in the agglomerate particle, e.g. by measuring the spatially resolved elemental composition via EDX in a scanning electron microscope.

It is also possible to analogously measure other, differing properties in the different homogeneous regions of the composite particle in a spatially resolved manner and draw on them as a criterion. For example, the spatially resolved Raman spectra of the individual homogeneous regions that are recorded by means of a Raman microscope can be compared with each other. Further, it is possible to record a spatially resolved mass spectrogram with a corresponding setup, e.g. sputtering by focused ion beam (FIB). In this case a composite particle could consist e.g. of respectively chemically identical substances with different isotope compositions, so that the evaluation involves rating the specific isotope types or isotope distributions in the different homogeneous regions.

Further, it is possible to draw on further analytical methods for measuring the optical properties or the elemental composition, instead of the preferred analytical methods (confocal laser microscope, SEM/EDX or SEM/WDX). For example, a spatially resolved measurement of the elemental composition would be measurable on a transmission electron microscope by EELS (electron energy loss spectroscopy). Likewise, there are devices for micro X-ray fluorescence analysis (μ-RFA) which can determine spatially resolved elemental compositions. As an alternative to confocal laser microscopy one might mention e.g. two-photon microscopy on a multiphoton microscope.

Embodiment Example 1 (Illuminant Agglomerate as the Only Security Feature)

A first luminescing illuminant, $SrAl_{12}O_{19}:Sm^{3-}$ (excitation 405 nm, emission sharp-band with several lines between 560 nm and 750 nm, lifetime approx. 2.7 ms) and a second luminescing illuminant, $KY_3F_{10}:Pr^{3+}$ (excitation 444 nm, emission sharp-band with several lines between 500 nm and 750 nm partly overlapping with the lines of the first illuminant, lifetime in the range of a few μs) are mixed in a quantity ratio of 1:1 and ground down to a D99 grain size of 5-6 μm with a simultaneous D50 grain size of 1.2-2.0 μm using an agitator ball mill.

For manufacturing the agglomerates, 245 g water is put in a thermostattable glass container and heated to 75° C. Thereupon 43 g potassium hydrogencarbonate is dissolved in warm water. While stirring, 33 g of the ground-down illuminant mixture is added and dispersed for 1 minute. Thereupon 207 g of a diluted aqueous potassium water glass solution is metered in at a speed of 3.5 g per minute, with the concentration of the potassium water glass solution being so selected that 15 g $SiO_2$ is deposited on the agglomerates. The product is filtered off, washed twice with 150 ml water and dried at 60° C. in a drying oven. There are obtained particle agglomerates with a D99 grain size of 18-20 μm and a simultaneous D50 grain size of 7-9 μm.

The manufactured agglomerates are so added to the raw papermaking material during sheet production that the agglomerates are contained in the resulting sheet with a mass fraction of 0.02 percent by weight.

For authentication, the existence of the added agglomerates in the value document is checked.

For this purpose, the sheet is examined by means of a confocal laser microscope. Upon excitation with a diode laser of the wavelength 405 nm, in particular the first luminescing illuminant is excited, as well as the background luminescence of the paper fibers, auxiliary agents and fillers, where applicable. Upon excitation with a second laser of the wavelength 440 nm, in particular the second illuminant is excited.

The two lasers (405 nm and 440 nm) are operated simultaneously. For imaging, a suitable objective (20×/NA0.8) is used. The field of view of 0.7 mm×0.7 mm with 1024×1024 pixels is scanned line by line, with the dwell time on a pixel being about 12 μs. The confocal pinhole is so adjusted that the resolution is 3 μm. At each image point the luminescent light is measured in a spectrally resolved manner. The thus obtained spectra are correlated with comparative spectra in an automated manner, so that the sought signal is separated from the fluorescent background and hereby probably positive detection events (target particles) can be identified. A positive detection event means that the particle was identified as an agglomerate of the two luminescing illuminants used, i.e. has contiguous regions with a size of at least five pixels, in which one of the two spectra belonging to the illuminants respectively dominates.

In the examined domain of 5×5 fields of view, eleven target particles were identified. Of said eleven target particles, nine proved to be positive detection events and two particles had to be discarded because they did not have regions of both illuminants or because the regions not were large enough.

By way of example, the procedure upon detailed analysis will be outlined for a positive and a negative detection event.

For detailed analysis on the target particle, the imaging parameters must be adapted suitably. For this purpose, the location of such a probably positive detection event is set in the center of the image. Image size (scan region), focal plane (z position), resolution (via the confocal pinhole) and laser powers are so adjusted that the target particle can be precisely examined for detection.

On the one target particle, three regions can be identified. Region 1 consists of seven pixels which can be unambiguously associated with the spectrum of the first luminescing illuminant, $SrAl_{12}O_{19}:Sm^{3+}$. Region 2 consists of nine pixels which can be unambiguously associated with the spectrum of the second luminescing illuminant, $KY_3F_{10}:Pr^{3+}$. The third contiguous region can again be spectrally associated with the first illuminant, $SrAl_{12}O_{19}:Sm^{3+}$, but only contains three contiguous pixels. By re-adapting the confocal pinhole to increase the resolution and by adapting the focal plane, one finds a setting in which said third region likewise has enough contiguous pixels, so that said region can also be drawn on for authentication. A region added through the changed focal position has no unambiguous spectral association, and a further added region is too small, having three pixels. The thus found and analyzed target particle thus constitutes an agglomerate of at least three primary particles of the two illuminants used and is a positive detection.

Another target particle must be discarded in the detailed analysis carried out as above, since it turns out that only a region with more than five contiguous pixels can be unambiguously associated with one of the two spectra. The other regions are too small or cannot be unambiguously associated spectrally.

To carry out the authentication by an alternative method, the sample is examined in a scanning electron microscope (SEM) by means of EDX after a preparatory method customary for the device. In a first image-producing step, possible positive detection events (target particles) are searched for. For this purpose, either the element contrast in the SEM image is drawn on, or an imaging EDX analysis is directly carried out by which the elements Y and Sr are searched for in a targeted manner. Said elements show suitable EDX signals for the first search. For authentication, the target particles are sought out, and a resolving EDX analysis carried out on said particles. For detection, there is to be detected on the particles the property that in separable regions of at least five contiguous pixels the two elements Sr and Al belonging to the first illuminant or the elements Y and F belonging to the second illuminant are found.

Upon the analysis of a target particle (illuminant agglomerate) on a scanning electron microscope in the imaging EDX mode, there can be identified a plurality of separate regions containing the elements yttrium and fluorine or strontium and aluminum. At the same time, silicon is ascertained on the total agglomerate. Since there can be ascertained sufficiently large separable regions respectively simultaneously containing two elements belonging together in the illuminants used, said agglomerate is deemed a positive detection. Further found agglomerates are examined and rated in this manner.

Embodiment Example 2 (Illuminant Agglomerate Together with Machine-Readable Feature)

A first luminescing $Y_3Al_5O_{12}$:Sm and a second luminescing $CaNb_2O_6$:Dy are mixed in a quantity ratio of 1:1 and ground to a grain size D99=5-6 μm and D50=1.2-2.0 μm.

10 g illuminant mixture is dispersed in 60 g water. 120 mL ethanol and 3.5 mL ammonia (25%) are added. While stirring with a blade agitator, 10 mL tetraethyl orthosilicate is slowly added and the reaction mixture stirred for eight more hours. The product is filtered off, washed twice with 40 mL water and dried at 60° C. in a drying oven. There are obtained particle agglomerates with a D99 grain size of 20-30 μm. The obtained agglomerates are tempered for one hour at 300° C. and thereupon treated with an ultra centrifugal mill. There is obtained a product with a reduced D99 grain size of 15-18 μm and a simultaneous D50 grain size of 7-8 μm.

5 g agglomerates is mixed with 95 g of a machine-readable luminophore-based security feature, for example the substance $Gd_{2.8}Fe_5O_{12}$:$Tm_{0.2}$ from Example 9 of the print WO 81/03507 A1, to obtain a machine-readable feature with a forensic component. The feature is thereupon so added to the paper pulp during sheet production that it is contained in the resulting sheet with a mass fraction of 0.4 percent by weight. The machine-readable feature can be checked at high speeds by corresponding specialized detectors in bank-note processing machines.

In case of need, however, a forensic examination can also be effected here to prove the authenticity of the bank note without any doubt, without requiring the identity and the corresponding detection parameters of the machine-readable security feature to be revealed.

The detection of the forensic feature proceeds as in Example (1). Upon rating of the luminescence properties by confocal laser microscopy, the influence of the machine-readable feature can be neglected since the emission lies in a different spectral region relative to the forensic feature. Upon authentication via EDX one can also draw on, in addition to the different elements of the two illuminants (in this example, in particular Al and Y for the first substance and Ca and Nb for the second substance) that are agglomerated into the forensic feature, the elements (here silicon) that are accumulated between or around the primary particles and consolidate the agglomerate.

Embodiment Example 3 (Non-Luminescing Substance Agglomerate)

A first non-luminescing substance $ZnAl_2O_4$ and a second non-luminescing substance $Zr_3(PO_4)_4$ are mixed in a quantity ratio of 1:1 and ground to a grain size D99=5-6 μm and D50=1.2-2.0 μm.

10 g of this mixture of substances is dispersed in 60 g water. 120 mL ethanol and 3.5 mL ammonia (25%) are added. While stirring with a blade agitator, 10 mL tetraethyl orthosilicate is slowly added and the reaction mixture is stirred for eight more hours. The product is filtered off, washed twice with 40 mL water and dried at 60° C. in a drying oven. There are obtained particle agglomerates with a D99 grain size of 20-30 μm. The obtained agglomerates are tempered for one hour at 300° C. and thereupon treated with an ultra centrifugal mill. There is obtained a product with a reduced D99 grain size of 15-18 μm and a simultaneous D50 grain size of 7-8 μm.

The manufactured agglomerates are thereupon so added to the paper pulp during sheet production that the agglomerates are contained in the resulting sheet with a mass fraction of 0.02 percent by weight.

The detection of the forensic feature via SEM/EDX proceeds as in Example (1), with in particular the joint occurrence of the elements Zn and Al being drawn on for detection of the first substance and the joint occurrence of the elements Zr and P for detection of the second substance.

Embodiment Example 4 (Illuminant Agglomerate with Quasi-Identical Emission of the Single Components but Different Decay Times and Element Distributions, and a Luminescing Camouflage Substance with Emissions in the Same Spectral Region)

A first substance $LaAlGe_2O_7$:$Eu_{0.005}$ with sharp-band luminescence in the red spectral region and a first decay time of approx. 1.9 ms, and a second spectrally quasi-identically luminescing substance $LaAlGe_2O_7$:$Eu_{0.2}$ with a second, different decay time of approx. 2.4 ms are mixed in a quantity ratio of 1:1 and ground down to a D99 grain size of 5-6 μm and a simultaneous D50 grain size of 1.2-2.0 μm using an agitator ball mill.

For manufacturing the agglomerates, 245 g water is put in a thermostattable glass container and heated to 75° C. Thereupon 43 g potassium hydrogencarbonate is dissolved in warm water. While stirring, 33 g of the ground-down mixture of substances is added and dispersed for 1 minute. Thereupon 207 g of a diluted aqueous potassium water glass solution is metered in at a speed of 3.5 g per minute, with the concentration of the potassium water glass solution being so selected that 15 g $SiO_2$ is deposited on the agglomerates. The product is filtered off, washed twice with 150 mL water and dried at 60° C. in a drying oven. There are obtained particle agglomerates with a D99 grain size of 18-20 μm and a simultaneous D50 grain size of 7-9 μm.

The agglomerates are compounded in a quantity ratio of 1:50 with the camouflage substance $Zn_{0.965}Ba_{0.025}S:Mn_{0.001}$ having broad-band luminescence in the red spectral region.

The manufactured mixture of camouflage substance and agglomerates is thereupon so added to the paper pulp during sheet production that the agglomerates are contained in the resulting sheet with a mass fraction of 0.015 percent by weight.

The detection of the forensic feature proceeds as in Embodiment example 1.

Embodiment Example 5 (Value-Document System, Encoded with Forensic Security Features)

A value-document system is constructed exploiting the properties "luminescence color" and "elemental composition", i.e. detection of both luminescence and elemental composition on the same selected particles:

1) Value-document sort 1, marked with agglomerate particles of yellow luminescing $ZnNb_2O_6:Dy^{3+}$ and red luminescing $Y_3Al_5O_{12}:Sm^{3+}$
2) Value-document sort 2, marked with agglomerate particles of yellow luminescing $Y_3Al_5O_{12}:Dy^{3+}$ and red luminescing $ZnNb_2O_6::Sm^{3+}$
3) Value-document sort 3, marked with agglomerate particles of yellow luminescing $ZnNb_2O_6:Dy^{3+}$ and red luminescing $ZnNb_2O_6::Sm^{3+}$
4) Value-document sort 4, marked with agglomerate particles of yellow luminescing $Y_3Al_5O_{12}:Dy^{3+}$ and red luminescing $Y_3Al_5O_{12}::Sm^{3+}$ The elements Y and Nb can be detected especially well by SEM/EDX here due to their high signal intensity.

This encoding system might be extended by additionally including further red or yellow luminescing illuminants based on Sm or Dy with different host lattices such as $YNbO_4$, $ZnAl_2O_4$, $ZnTa_2O_6$ or $Y_2O_2S$.

The invention claimed is:

1. A security feature for safeguarding value documents, comprising agglomerate particles which are composed of at least two different, spatially separate solid homogeneous phases, wherein each of the phases is detectable, separable and identifiable in a spatially resolved manner only by means of a spatially resolving spectroscopic measuring method that is adapted for resolving down to the single-particle level, wherein the agglomerate particles are composed of two different, spatially separate solid homogeneous phases of which the first homogeneous phase is based on a first luminescing substance and the second homogeneous phase is based on a second luminescing substance, wherein the two luminescing substances have the same emission wavelengths but different excitation wavelengths and/or decay times and/or rise times.

2. The security feature according to claim 1, wherein the at least two different, spatially separate solid homogeneous phases comprise luminescing substances which emit in the visible spectral region.

3. The security feature according to claim 1, wherein the luminescing substances have a different excitation wavelength.

4. The security feature according to claim 1, wherein the agglomerate particles have a D99 grain size in a range of 1 micrometer to 30micrometers.

5. The security feature according to claim 1, wherein the agglomerate particles have a D50 grain size in a range of 1 micrometer to 30 micrometers.

6. The security feature according to claim 1, wherein the solid homogeneous phases composing the agglomerate particles respectively have a (D99) grain size in a range of 3 micrometers to 15 micrometers.

7. The security feature according to claim 1, wherein the solid homogeneous phases composing the agglomerate particles respectively have a grain size in a range of 1 micrometer to 8 micrometers.

8. The security feature according to claim 1, wherein the agglomerate particles are composed of two different, spatially separate solid homogeneous phases of which the first homogeneous phase is based on a first luminescing substance and the second homogeneous phase is based on a second luminescing substance, wherein the two luminescing substances have different rise times and/or decay times.

9. The security feature according to claim 2, wherein the luminescing agglomerate particles are so constituted that the luminescence emission of each individual phase has a complex spectrum consisting of at least two sharp bands and the spectrum is an emission spectrum in the range of 400 to 750 nm.

10. The security feature according to claim 1, wherein the agglomerate particles are composed of two different, spatially separate solid homogeneous phases of which the first homogeneous phase is based on a first luminescing substance with a rise time >2 µs.

11. The security feature according to claim 1, wherein the agglomerate particles are composed of two different, spatially separate solid homogeneous phases of which the first homogeneous phase is based on a first luminescing substance and the second homogeneous phase is based on a second luminescing substance, wherein the two luminescing substances have the same luminescence properties but mutually differ with regard to their elemental compositions.

12. The security feature according to claim 1, wherein additionally at least one camouflaging substance is added which does not consist of composite particles itself and has similar properties to the agglomerate particles under the analytical method utilized for detection, and in particular in the case of a luminescing agglomerate particle with sharp-band emission in a certain spectral region shows broad-band luminescence in said spectral region.

13. A value document having a security feature according to claim 1.

14. The value document according to claim 13, wherein the security feature is incorporated into the volume of the value document and/or applied to the value document.

15. The value document according to claim 13, wherein the share of the security feature in the value document lies in a range of 0.001 to 0.1 percent by weight.

16. The value document according to claim 13, wherein the agglomerate particles are contained in the value document with an area density such that in the particle-size range of 4 micrometers to 20 micrometers there are contained particle numbers of 1 to 1000 particles per square millimeter.

17. A method for checking the authenticity of the value document according to claim 13, comprising the step of spatially resolved detecting, separating and identifying of the at least two different, spatially separate solid homogeneous phases contained in the agglomerate particles by means of at least one spatially resolving spectroscopic measuring method that is adapted for resolving down to the single-particle level and reliably separating the phases spectrally.

18. The method according to claim 17, wherein the spatially resolving analytical method is selected from the group consisting of confocal laser microscopy, multiphoton microscopy, fluorescence lifetime microscopy, spatially resolved X-ray diffraction, spatially resolved Raman scattering, scanning electron microscopy with energy-dispersive X-ray spectroscopy and spatially resolved X-ray fluorescence analysis.

19. A method for safeguarding a value document, comprising the following steps:
   a) predetermining at least one spatially resolving spectroscopic measuring method;
   b) selecting at least two solid homogeneous phases having at least one property distinguishable by the spatially resolving spectroscopic measuring method;
   c) combining the at least two solid homogeneous phases into agglomerate particles;
   d) incorporating and/or applying the agglomerate particles into or onto the value document as a security feature;
   e) detecting the substructure of the agglomerate particles in a spatially resolved manner and reliably separating the spectroscopic properties of the homogeneous phases by means of the predetermined spatially resolving spectroscopic measuring method;
   f) rating the authenticity of the value document using the data obtained in step e);
wherein the agglomerate particles are composed of at least two different, spatially separate solid homogeneous phases of which the first homogeneous phase is based on a first luminescing substance and the second homogeneous phase is based on a second luminescing substance, wherein the two luminescing substances have the same emission wavelengths but different excitation wavelengths and/or decay times and/or rise times.

20. The method according to claim 19, wherein the security feature is defined for safeguarding value documents, and each of the at least two different, spatially separate solid homogeneous phases is detectable, separable and identifiable in a spatially resolved manner only by means of a spatially resolving spectroscopic measuring method that is adapted for resolving down to the single-particle level.

21. Use of the security feature according to claim 1 as a forensic security feature in a value document, i.e. for value-document authentication based on the analysis of single particles by spatially resolved microscopic, spectroscopic methods, wherein the share of the security feature in the value document lies in a range of 0.001 to 0.1 percent by weight.

22. The use according to claim 21, wherein the agglomerate particles are contained in the value document with an area density such that in the particle-size range of 4 micrometers to 20 micrometers there are contained particle numbers of 1 to 1000 particles per square millimeter.

23. A value-document system having at least first value documents, e.g. of a first denomination, containing first agglomerate particles and second value documents, of a second denomination, containing second agglomerate particles, wherein the first and second value documents are respectively defined according to claim 13, wherein the first and second value documents can be distinguished on the basis of at least one of the spatially separate solid homogeneous phases by one or more predetermined spatially resolving spectroscopic measuring methods.

24. The value-document system according to claim 23, wherein the distinguishable properties are selected from luminescence emission wavelength, luminescence excitation wavelength, time behavior of the luminescence, elemental composition, three-dimensional form, isotope ratio, oscillation spectrum, crystal structure, magnetic properties.

25. A security feature for safeguarding value documents, comprising agglomerate particles which are composed of at least two different, spatially separate solid homogeneous phases, wherein each of the phases is detectable, separable and identifiable in a spatially resolved manner only by means of a spatially resolving spectroscopic measuring method that is adapted for resolving down to the single-particle level,
wherein the luminescing agglomerate particles are so constituted that the luminescence emission of each individual phase has a complex spectrum consisting of at least two sharp bands and the spectrum is an emission spectrum in the range of 400 to 750 nm, wherein the complex spectra of the individual phases mutually overlap, i.e. they are not congruent but differ in their shape, namely, peak position and/or peak shape and/or peak width in a range of 1 nm to 30 nm.

* * * * *